US009089259B2

(12) United States Patent
Takeuchi

(10) Patent No.: US 9,089,259 B2
(45) Date of Patent: Jul. 28, 2015

(54) ENDOSCOPE

(71) Applicant: OLYMPUS MEDICAL SYSTEMS CORP., Tokyo (JP)

(72) Inventor: Yasuo Takeuchi, Hachioji (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 25 days.

(21) Appl. No.: 13/712,553

(22) Filed: Dec. 12, 2012

(65) Prior Publication Data

US 2013/0178705 A1    Jul. 11, 2013

Related U.S. Application Data

(63) Continuation of application No. PCT/JP2012/056443, filed on Mar. 13, 2012.

(30) Foreign Application Priority Data

Mar. 25, 2011    (JP) .................................. 2011-066904

(51) Int. Cl.
   *A61B 1/00*    (2006.01)
   *A61B 1/005*    (2006.01)
   *G02B 23/24*    (2006.01)

(52) U.S. Cl.
   CPC ............. *A61B 1/0051* (2013.01); *A61B 1/0052* (2013.01); *A61B 1/0055* (2013.01); *A61B 1/00078* (2013.01); *G02B 23/2476* (2013.01); *A61B 1/0057* (2013.01)

(58) Field of Classification Search
   CPC .............................. A61B 1/0051; A61B 1/0057

USPC .................................................. 600/144, 146
See application file for complete search history.

(56) References Cited

U.S. PATENT DOCUMENTS

| 4,267,828 A | * | 5/1981 | Matsuo | 600/138 |
| 4,329,980 A | * | 5/1982 | Terada | 600/144 |
| 4,971,033 A | * | 11/1990 | Ehlers | 600/139 |

(Continued)

FOREIGN PATENT DOCUMENTS

| JP | A-10-127569 | 5/1998 |
| JP | A-10-201703 | 8/1998 |

(Continued)

OTHER PUBLICATIONS

International Search Report issued in International Application No. PCT/JP2012/056443 dated Jun. 12, 2012 (with translation).

(Continued)

*Primary Examiner* — Anhtuan T Nguyen
*Assistant Examiner* — Jae Woo
(74) *Attorney, Agent, or Firm* — Oliff PLC

(57) ABSTRACT

An endoscope includes an insertion section, a bending section, a bending operation section and a shift mechanism. The bending section includes a first bending section and a second bending section provided at a proximal end of the first bending section. The second bending section includes an actuation pipe interposed between an angle wire extending in the second bending section and a wire guide through the angle wire and guiding the angle wire, and supported to be moved in the extending direction of the wire guide with respect to the wire guide. A rigidity of the second bending section is shifted while the actuation pipe is moved in the extending direction of the wire guide.

6 Claims, 9 Drawing Sheets

(56) References Cited

U.S. PATENT DOCUMENTS

| | | | |
|---|---|---|---|
| 5,025,778 A * | 6/1991 | Silverstein et al. | 600/104 |
| 5,125,395 A * | 6/1992 | Adair | 600/121 |
| 5,168,864 A * | 12/1992 | Shockey | 600/144 |
| 5,733,245 A * | 3/1998 | Kawano | 600/144 |
| 5,810,715 A * | 9/1998 | Moriyama | 600/144 |
| 5,885,208 A * | 3/1999 | Moriyama | 600/144 |
| 5,976,074 A * | 11/1999 | Moriyama | 600/144 |
| 6,551,238 B2 * | 4/2003 | Staud | 600/121 |
| 8,133,171 B2 * | 3/2012 | Barry et al. | 600/151 |
| 8,366,606 B2 * | 2/2013 | Watanabe et al. | 600/144 |
| 2006/0058582 A1 * | 3/2006 | Maahs et al. | 600/144 |
| 2007/0043261 A1 * | 2/2007 | Watanabe et al. | 600/144 |
| 2009/0326326 A1 * | 12/2009 | Lin et al. | 600/146 |
| 2010/0036202 A1 * | 2/2010 | Lin et al. | 600/146 |
| 2010/0280320 A1 | 11/2010 | Alvarez et al. | |
| 2011/0295069 A1 * | 12/2011 | Ouchi | 600/146 |
| 2012/0265016 A1 * | 10/2012 | Katsura et al. | 600/146 |

FOREIGN PATENT DOCUMENTS

| | | |
|---|---|---|
| JP | A-2003-116779 | 4/2003 |
| JP | A-2003-126024 | 5/2003 |
| JP | A-2007-054125 | 3/2007 |
| JP | A-2007-061377 | 3/2007 |
| JP | B2-4914952 | 1/2012 |

OTHER PUBLICATIONS

English-language Translation of the Written Opinion of the International Searching Authority issued in International Application No. PCT/JP2012/056443 dated Jun. 12, 2012.

Oct. 10, 2013 English Translation of the International Preliminary Report on Patentability issued in International Application No. PCT/JP2012/056443.

Apr. 11, 2014 Supplementary European Search Report issued in European Patent Application No. 12 76 4238.

* cited by examiner

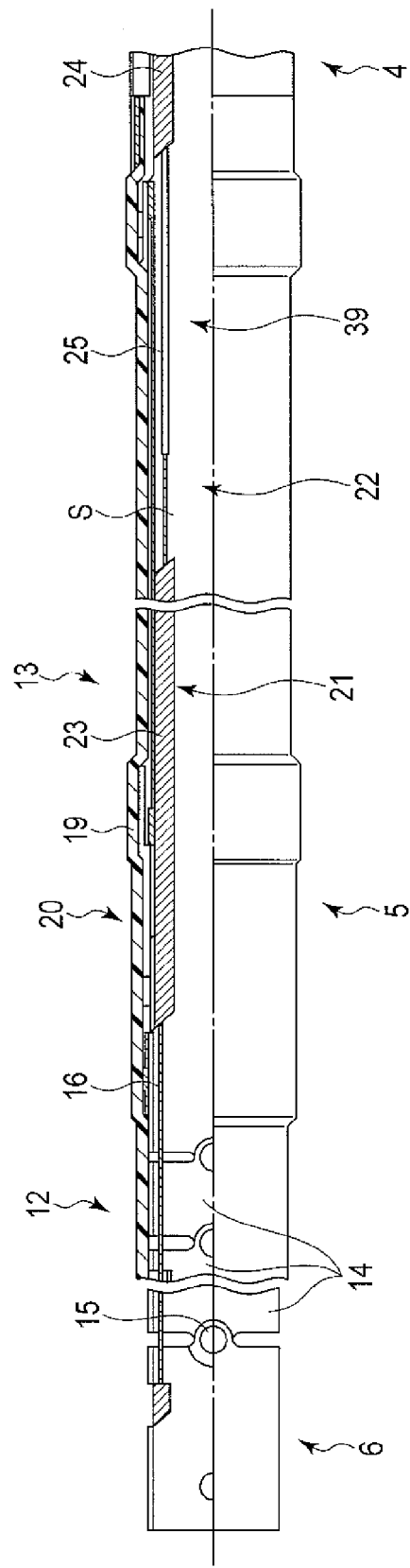
F I G. 2A

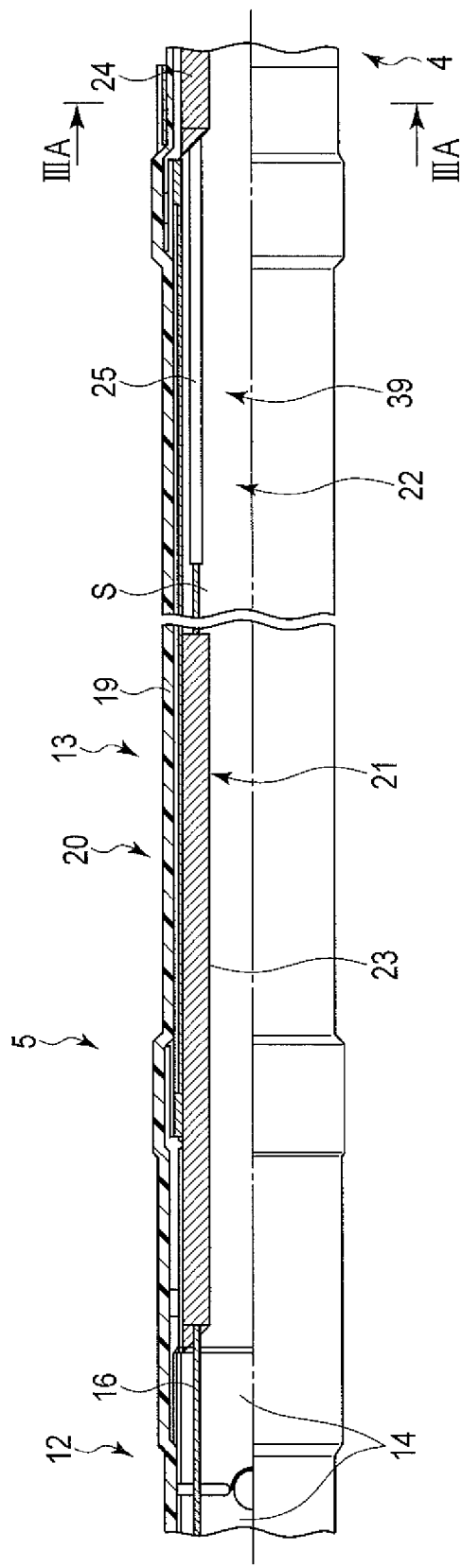
F I G. 2B

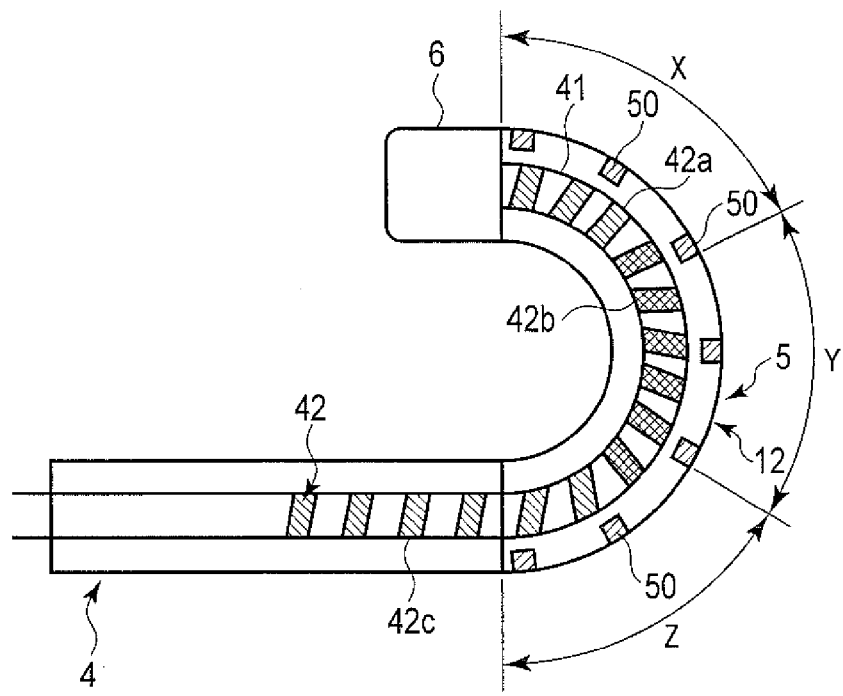
F I G. 6
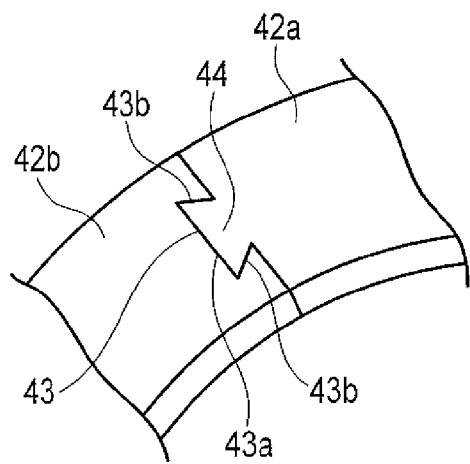
F I G. 7

ENDOSCOPE

CROSS-REFERENCE TO RELATED APPLICATIONS

This application is a Continuation Application of PCT Application No. PCT/JP2012/056443, filed Mar. 13, 2012 and based upon and claiming the benefit of priority from prior Japanese Patent Application No. 2011-066904, filed Mar. 25, 2011, the entire contents of all of which are incorporated herein by reference.

BACKGROUND OF THE INVENTION

1. Field of the Invention

This invention relates to an endoscope including a bending section.

2. Description of the Related Art

Endoscopes generally include a bending section at the distal end of the insertion section inserted into a body cavity, and flexible endoscopes or rigid endoscopes, each having a bending section, such as a bending lever operated to bend the bending section, at the operation section coupled to the insertion section. In the small diameter flexible endoscopes, such as bronchoscopes inserted into the bronchi, a bending section is provided at the distal end of a small diameter flexible tubular section, and a distal end rigid section is provided at the distal end of the endoscope. In the flexible tubular section, a metal mesh tube (braid) is mounted on an outer circumferential surface of a metal helical tube (flex), and a resin outer coat is mounted on the outer circumferential surface of the metal mesh tube. Therefore, the flexible tubular section can be flexibly bent according to a shape of an insertion path.

In the bending section, a plurality of bending pieces is collaterally arranged in the central axis direction of the insertion section. One end of operation wires are coupled to a distal end of a most distal end bending piece among the bending pieces. The other end of the operation wires extend toward the operation section and are coupled to the bending operation section, such as a bending lever. Wire guides through the wire are placed in the flexible tubular section. Distal ends of the wire guides are secured to the distal end of the flexible tubular section. As the bending lever is rotated, the operation wire is pulled, applying a traction force to the most distal bending piece. The bending pieces of the bending section are therefore turned around their each rotation axis. The bending section is thereby arched as a whole. The illumination window, the observation window and the opening of the instrument insertion channel provided at the distal end rigid section are therefore directed in any desired direction.

Jpn. Pat. Appln. KOKAI Publication No. 2007-61377 discloses a configuration in which a flexible section being shorter than the bending section and able to bend in any desired direction is provided between the distal end rigid section and the bending section, and a flexible-section bending means for bending the flexible section is provided in the operation section. Herein, the flexible-section bending means bends the flexible section by a remote-control. If it receives an external force, the flexible section remains rigid and is not bendable, or the flexible section can be bent according to the external force, when the remote-control of the flexible-section bending means is not performed. Hence, the flexible section can be switched to any one of three states, i.e., bendable by the flexible-section bending means, not bendable by the flexible-section bending means, and freely bendable if it receives an external force.

Jpn. Pat. Appln. KOKAI Publication No. 2003-116779 discloses an endoscope having a flexible tubular section that can be changed in stiffness. A wire and a coil are inserted into the flexible tubular section. In the flexible tubular section, a distal end of the wire is secured at a proximal end of the bending section. In the flexible tubular section, a distal end of the coil is secured adjacent to the distal end of the wire, and a proximal end of the coil is prevented by a coil stopper from moving backwards. The proximal end of the wire extending backwards from the rear end of the coil is pulled, as a rigidity adjusting knob is rotated at the operation section. At the same time, the wire stopper provided at the rear end of the coil is moved as the rigidity adjusting knob is rotated. So moved, the coil is compressed, thus the rigidity of the flexile tubular section is adjusted.

BRIEF SUMMARY OF THE INVENTION

According to an aspect of the present invention, an endoscope is characterized by including: an elongate insertion section; a bending section which is provided at a distal end of the insertion section and configured to be bent; a bending operation section configured to operate a bending of the bending section; a shift mechanism configured to shift a bend radius of the bending section depending on the bending operation section; and a shift operation section configured to arbitrarily operate the shift mechanism, wherein the bending section comprises a first bending section configured to bend and a second bending section provided at a proximal end of the first bending section and configured to bend, the second bending section comprises an actuation pipe interposed between an angle wire extending in the second bending section and a wire guide through the angle wire and guiding the angle wire, and supported to be moved in the extending direction of the wire guide with respect to the angle guide, and a rigidity of the second bending section is configured to be shifted while the actuation pipe is moved in the extending direction of the wire guide.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2A is a longitudinal sectional view of major components, showing the coupling part of the bending section of the endoscope according to the first embodiment;

FIG. 2B is a longitudinal sectional view of major components, showing the bending section of the endoscope, which can be bent and deformed;

FIG. 6 is a side view schematically showing the configuration of the forceps channel built in the insertion section of the endoscope according to the first embodiment;

FIG. 7 is a perspective view of major components, showing a connection part of the reinforcing coil in the instrument insertion channel of the endoscope according to the first embodiment.

DETAILED DESCRIPTION OF THE INVENTION

First Embodiment (Configuration)

Figure 1A:
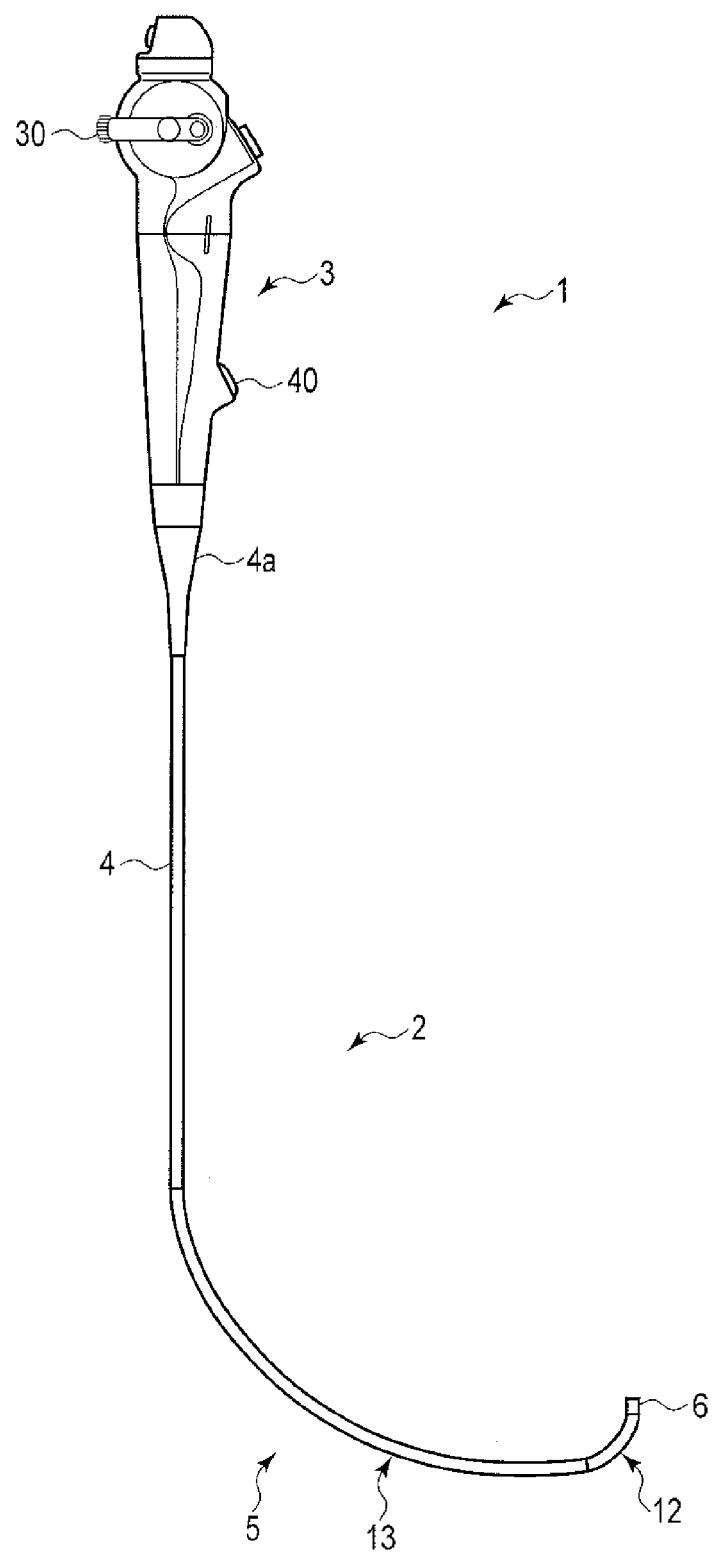
FIG. 1A is a side view schematically showing the overall configuration of an endoscope according to a first embodiment of this invention.

FIG. 1A to FIG. 7 show a first embodiment of this invention. FIG. 1A shows the overall configuration of a small diameter flexible endoscope 1, such as a bronchoscope. The endoscope 1 includes an elongate insertion section 2 configured to be inserted into a body cavity, a thick operation section 3 coupled to the proximal end of the insertion section 2, and a universal cable (not shown) extending from the side of the operation section 3. The One end of the universal cable is removably connected to a light source device by a connector.

Figure 1B:
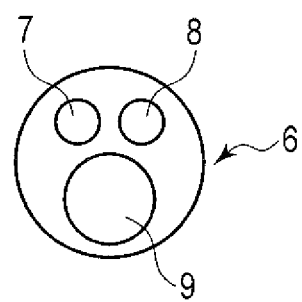
FIG. 1B is a front view of the distal end rigid section.

In the insertion section 2, a bending section 5 is provided at a distal end of a flexible tubular section 4, and a distal end rigid section 6 is provided at the most distal end of the insertion section 2. As shown in FIG. 1B, such as an illumination window 7, an observation window 8, and an opening 9 of an instrument insertion channel are arranged at the distal end rigid section 6. A distal end of a light guide 10 (see FIG. 3A and FIG. 3E) is connected to the back of the illumination window 7. An imaging element, e.g., CCD (not shown) is arranged to the backward of the observation window 8.

Figure 3A:
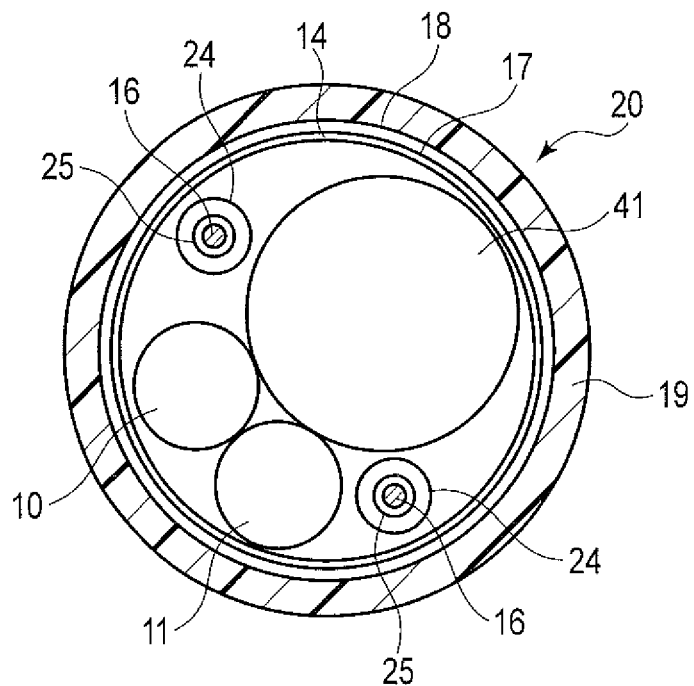
FIG. 3A is a sectional view taken along line IIIA-IIIA shown in FIG. 2B.
Figure 3B:
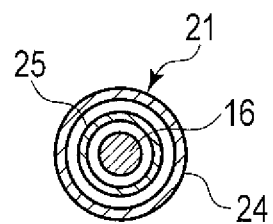
FIG. 3B is a transverse sectional view showing a configuration state of an angle wire, an actuation pipe and an angle coil.

As shown in FIG. 3A and FIG. 3B, the light guide 10 and a signal cable 11 are inserted into the insertion section 2, the operation section 3, and the universal cable. The rear end of the light guide 10 is connected by a light guide connector to the light source device. The rear end of the signals cable 11 is connected to an external camera control unit (CCU) by an electrical connector (not shown). The light guide 10 receives the light emitted from the light source device and guides the light to the illumination window 7. The light forward radiates from the illumination window 7 of the distal end rigid section 6, and illuminates an object such as an affected part. The objective lens secured to the observation window focuses the image of the object so illuminated, at the imaging element. The image is converted to an electric signal by the imaging element. The electric signal is transmitted from the imaging element to an external camera control unit through the signal cable 11. The signal processing circuit incorporated in the camera control unit converts the signal to a video signal of a standard type. The video signal is output to the monitor connected to the camera controller. The monitor displays the image observed through the endoscope 1.

The flexible tubular section 4 includes a helical tube (i.e., flex) made by helically winding a metal strip-shaped plate (not shown), a metal mesh tube (braid) mounted on the surface of the helical tube, and a resin outer coat mounted on the outer circumferential surface of the metal mesh tube. Therefore, the flexible tubular section 4 can be flexibly bent according to a shape of an insertion path. A proximal end of the flexible tubular section 4 is coupled to a distal end of the operation section 3. A tapered breakage-preventing member 4a with breakage-preventing function is provided on the outer circumferential surface of the proximal end of the flexible tubular section 4.

FIG. 2A is a longitudinal sectional view of major components, showing the coupling part of the bending section 5 of the endoscope according to this embodiment. The bending section 5 according to this embodiment includes an active bending section (first bending section) 12 arranged at the distal side thereof and bent as desired, and a passive bending section (second bending section) 13 provided at the proximal side of the active bending section 12 and held with a state that is passively bent with an external force.

A plurality of ring-shaped bending pieces 14 are collaterally arranged in the active bending section 12 in the central axis direction of the insertion section 2. Any back and forth adjacent bending pieces 14 are coupled together with shafts 15 such as a pair of rivets, and can rotate with respect to each other. Each of a distal end of two angle wires 16 is coupled to the distal end of the most distal bending piece 14 or to the rear end of the distal end rigid section 6. The two angle wires 16 are spaced apart from each other by about 180° in the circumferential direction of the bending pieces 14. In the active bending section 12 of this embodiment, the two angle wires 16 are located along upward and downward, or leftward and rightward, the distal end rigid section 6 can be bent to two directions. Nonetheless, if the active bending section 12 is designed to bend the distal end rigid section 6 in four directions, upward, downward, leftward or rightward, four angle wires 16 are used, one spaced apart from the next one by 90°. Each of the rear-end parts of the angle wires 16 extends to the operation section 3. The each of two or four angle wires 16 may be used, one spaced apart from the other or next one by an angle other than 90°.

As shown in FIG. 3A, the passive bending section 13 include a flexible tube body 20 including a metal helical tube (flex) 17, a metal mesh tube (braid) 18 mounted on the surface of the metal helical tube 17, and an outer coat 19 made of rubber and mounted on the outer circumferential surface of the mesh tube 18. The distal end of the outer coat 19 of the passive bending section 13 extends to the active bending section 12 and is formed integral with the active bending section 12.

The tube body 20 of passive bending section 13 has almost the same configuration as the flexible tubular section 4. The tube body 20 of passive bending section 13, however, differs from the flexible tubular section 4 in the manner of winding a metal strip constituting the helical tube 17, the width and thickness of the metal strip, and in the configuration of mesh tube 18. The tube body 20 of the passive bending section 13 and the flexible tubular section 4 can be adjusted in flexibility, as needed. Thus, the tube body 20 of the passive bending section 13 can be made harder than, more flexible than or as flexible as, the flexible tubular section 4, in accordance with the object into which the insertion section 2 of the endoscope 1 is inserted. A distal end of an angle coil (wire guide unit) 21 is secured to the inner circumferential surface of the distal part of the tube 20 of the passive bending section 13. The angle wire 16 is inserted into the angle coil (wire guide unit) 21 and is guided therein. The angle coil 21 is formed of a close metal coil.

A bending shape adjusting section (shift mechanism) 22 which can permit to change the bend form (i.e. the bend radius) of the tube body 20 of the passive bending section 13 is provided in the tube body 20 of the passive bending section 13. The bending shape adjusting section 22 includes a front side coil (front side wire guide section) 23 and a rear side coil (rear side wire guide section) 24, which are formed by splitting the angle coil 21 into a front side and a rear side in the passive bending section 13. The distal end of the front side coil 23 is secured to the distal end of the passive bending section 13. The proximal end of the front side coil 23 extends in the passive bending section 13 for a given distance. The distal end of the rear side coil 24 is secured to the rear end of the passive bending section 13. The proximal end of the rear side coil 24 extends to the rear end of the insertion section 2. As a result, a space is formed between the front side coil 23 and the rear side coil 24. In the space, a gap S between the proximal end of the front side coil 23 and a distal end of an actuation pipe 25 may be adjusted, as is discussed in further detail below.

The actuation pipe 25 is provided between the angle wire 16 extending in the passive bending section 13 and the angle coil 21 through which the angle wire 16 is inserted and guided, and can move with respect to the angle coil 21 in the extending direction of the angle coil 21. The actuation pipe 25 is made of a metal having hyperelasticity and inserts into the rear side coil 24. A length of the actuation pipe 25 is a same length or longer than that of the rear side coil 24. The outside diameter of the actuation pipe 25 is a same inside diameter or larger than the inside diameter of the front side coil 23. Therefore, the actuation pipe 25 will never be inserted into the front side coil 23. In the bending shape adjusting section 22, the rigidity of the passive bending section 13 is adjusted when the actuation pipe 25 is moved to adjust the gap S in the extending direction of the angle coil 21.

Figure 4:
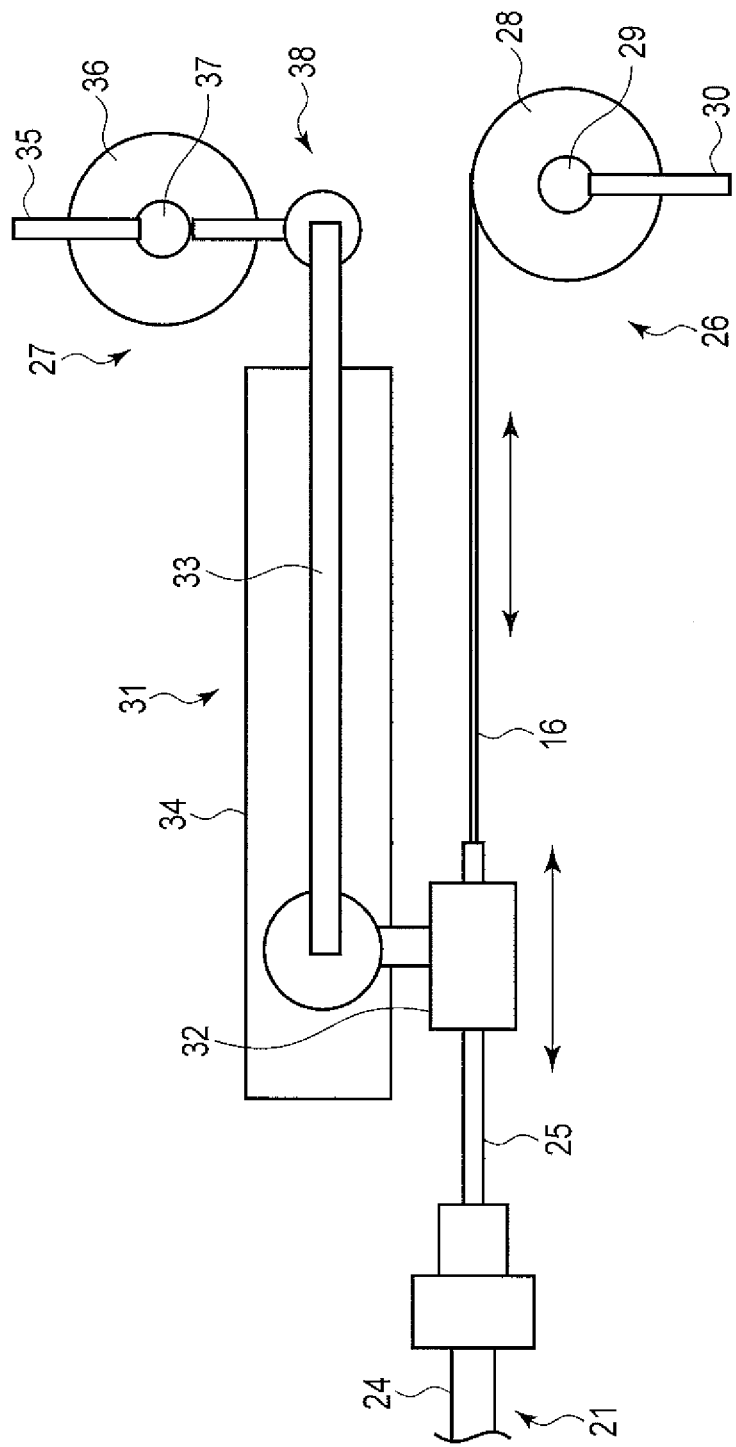
FIG. 4 is a side view schematically showing the configurations of the wire operating unit and actuation-pipe operating section of the endoscope according to the first embodiment.

As shown in FIG. 4, a wire operating section 26 to pull the angle wire 16, and an actuation pipe operating section 27 to pull the actuation pipe 25 is provided on the operation section 3. A rotary drum 28 to which the rear end of the angle wire 16 is coupled is provided on the wire operating section 26. A bending operation lever (bending operation section) 30 is attached to a rotary shaft 29 of the rotary drum 28.

As the bending operation lever 30 is rotated, one of the pair of the angle wires 16 provided along the upward and downward, or leftward and rightward is pulled, while the other angle wire 16 is slackened. The active bending section 12 can thereby be bent toward the angle wire thus pulled.

A drive mechanism 31 to move the actuation pipe 25 in the extending direction of the angle coil 21 is provided on the actuation pipe operating section 27. The drive mechanism 31 includes a coupling member 32 fixed to the rear end of the actuation pipe 25, a connecting rod 33 secured at one end to the coupling member 32, a guide rail 34 guiding the connecting rod 33 in the movable direction of the actuation pipe 25, and a bend-form setting lever (variable operation member) 35 operated to set the bending form of the passive bending section 13. The bend-form setting lever 35 is mounted to a rotary drum 36. A drive force transmitting section 38 which converts the rotation operation of the bend-form setting lever 35 to a force that moves the connection rod 33 in the movable direction of the actuation pipe 25 is provided to a rotation shaft 37 of the rotary drum 36.

When the bend-form setting lever 35 is rotated, the actuation pipe 25 can be moved by the connection rod 33 and coupling member 32 to the extending direction of the angle coil 21. As the actuation pipe 25 is so driven, the gap S for the bending shape adjustment between the front side coil 23 and rear side coil 24 of the passive bending section 13, can be opened and closed, thus, the rigidity of the passive bending section 13 can be shifted.

In the bending shape adjusting section 22, the gap S is greatly widened when the actuation pipe 25 is pulled toward a side of the operation section 3 with the bent-form setting lever 35 of the actuation pipe operating section 27. In this case, the rigidity of the passive bending section 13 is shifted to be reduced, whereby the passive bending section 13 can be deformed in a state that the bend radius R of the passive bending section 13 is reduced, as shown at (III) in FIG. 5. In the state (first state) shown at (III) in FIG. 5, when the bending shape adjusting section 22 as a variable mechanism is operated by the bend-form setting lever 35 as a variable operation section, the active bending section 12 as a first bending section is bent together with the passive bending section 13 as a second bending section.

Further, the gap S is lessened when the actuation pipe 25 is pushed toward the active bending section 12 with the bend-form setting lever 35. In this case, the rigidity of the passive bending section 13 is shifted to be increased, whereby the passive bending section 13 can be deformed in a state that the bend radius R of the passive bending section 13 is increased, as shown at (I) in FIG. 5. In the state (second state) shown at (I) in FIG. 5, when the bending shape adjusting section 22 as a variable mechanism is operated by the bend-form setting lever 35 as a variable operation section, the passive bending section 13 as a second bending section is not bent while the active bending section 12 as a first bending section is bent.

Figure 5:
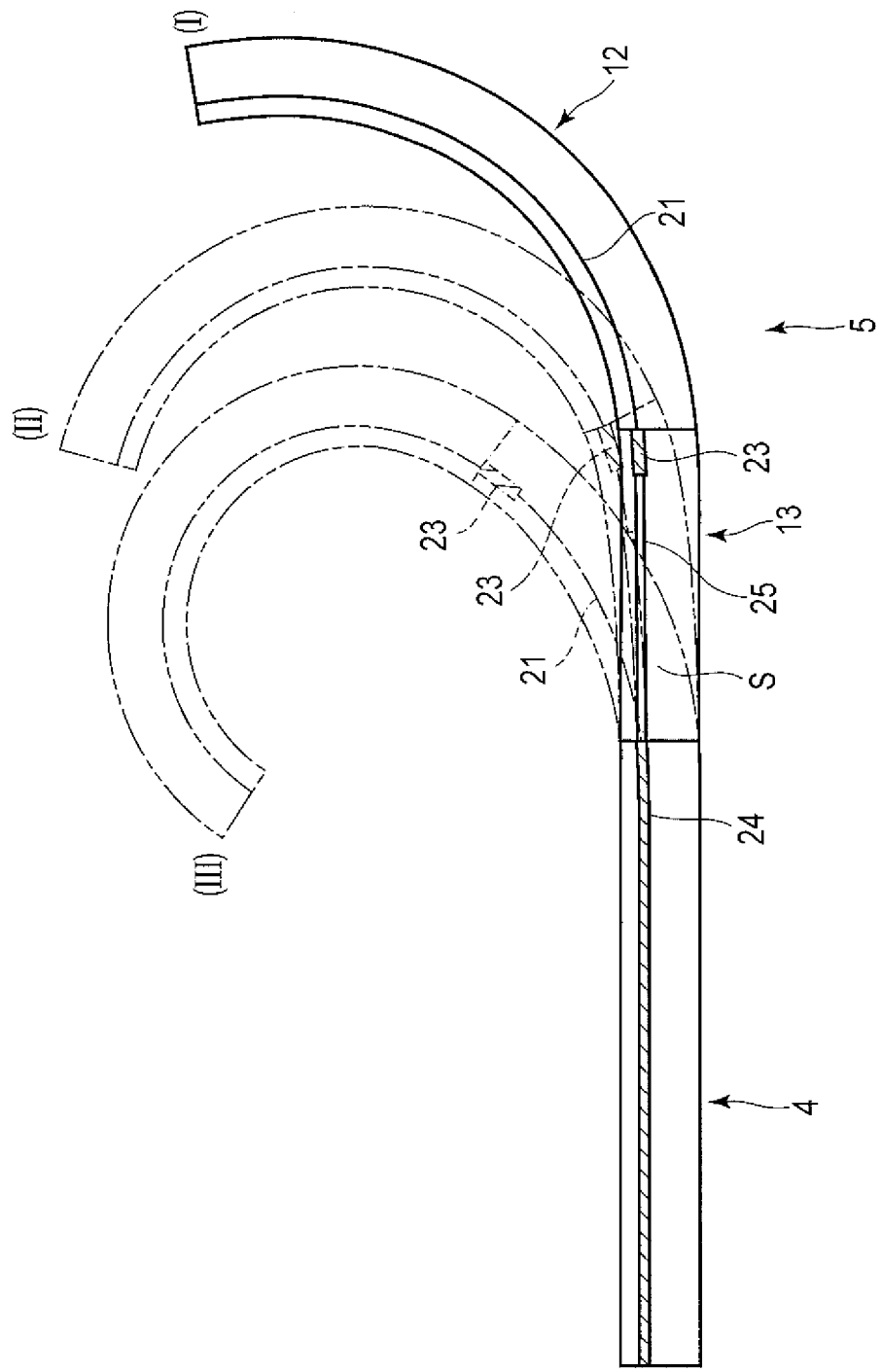
FIG. 5 is an explaining diagram explaining a deformation state of a curved shape in the passive bending section of the bending section of the endoscope according to the first embodiment.

The passive bending section 13 can be deformed to have such an intermediate bend radius R as shown at (II) in FIG. 5, when the actuation pipe 25 is moved to a midpoint of the space between the front side coil 23 and the rear side coil 24 with the bend-form setting lever 35.

The bending shape adjusting section 22 can shift the rigidity of the passive bending section 13 such that the passive bending section 13 permits to be bent by an operation of the bending operation lever 30 in the first state as shown at (III) or (II) in FIG. 5. The bending shape adjusting section 22 can shift the rigidity of the passive bending section 13 such that the passive bending section 13 such that the passive bending section 13 cannot permit to be bent by an operation of the bending operation lever 30 in the second state as shown at (I) in FIG. 5.

A bending rigidity variable mechanism 39 is formed in the bending shape adjusting section 22 to allow shifting the rigidity of the passive bending section 13 to a desired state, while the bend-form setting lever 35 of the actuation pipe operating section 27 is operated and shifts the actuation pipe 25 in the extending direction of the angle coil 21. When the bending rigidity variable mechanism 39 is operated, the bent form of the passive bending section 13 can be shifted as desired.

The operation section 3 includes an instrument insertion port 40. An instrument insertion channel 41 (see FIG. 3A and FIG. 3B) provided in the insertion section 2 is connected to the instrument insertion port 40. An instrument is inserted from the instrument insertion port 40 through the instrument insertion channel 41. Thereafter, the distal end of the instrument may be projected from the channel outlet port 9 of the distal end rigid section 6, so that the instrument can treat.

As shown in FIG. 6, a reinforcing coil 42 made of a metal strip wound helically is wound around the outer circumferential surface of the instrument insertion channel 41. The reinforcing coil 42 is a reinforcing member preventing the channel 41 from collapsing and clamped between a forceps and the wire guide 50 of the bending section 5 and being worn, as the instrument is inserted into the instrument insertion channel 41.

The reinforcing coil 42 can shift the stiffness of the coil according to a position of the bending section 5. That is, the reinforcing coil 42 includes three reinforcing coil parts 42a, 42b, and 42c that differ in stiffness, and the reinforcing coil part 42a is provided in the distal section X of the bending section 5, the reinforcing coil part 42b is provided in the middle section Y and the reinforcing coil part 42c is provided in the proximal section Z of the bending section 5, respectively. The three reinforcing coil parts 42a, 42b and 42c are respectively connected.

The first reinforcing coil part 42a, which is more flexible than a reinforcing coil of the standard rigidity, is provided at a part corresponding to the distal section X of the bending section 5. The second reinforcing coil part 42b, which is harder than the reinforcing coil of the standard rigidity, is provided at a part corresponding to the middle section Y of the bending section 5. The third reinforcing coil part 42c, which is more flexible than the reinforcing coil of the standard stiffness, is provided at a part corresponding to the proximal section Z of the bending section 5. The first reinforcing coil part 42a and the third reinforcing coil part 42c may include the same stiffness.

FIG. 7 shows a connection section between the first reinforcing coil part 42a and the second reinforcing coil part 42b. The second reinforcing coil unit 42b includes a coupling concave section 43 at one end thereof. The coupling concave section 43 includes tapered inclined surfaces 43b at both sides thereof, gradually widening toward the bottom 43a. The first reinforcing coil part 42a includes, at one end, a coupling convex section 44 shaped complementary to, and fitted in, the coupling concave section 43 of the second reinforcing coil 42b. The coupling convex section 44 in the one end of the first reinforcing coil part 42a is abutted on, fitted in, and connected to the coupling concave section 43 in the one end of the second reinforcing coil part 42b. A thin tube is wrapped with an outer circumference of a connection section of the first and second reinforcing coil parts 42a and 42b, the first and second reinforcing coil parts 42a and 42b is prevented from being disconnected from each other. Note that the second reinforcing coil part 42b and the third reinforcing coil part 42c are connected together in the same way as the first and second reinforcing coil parts 42a and 42b are connected.

(Operation)

Next, how the configuration described above operates will be explained. While using the endoscope 1 according to this embodiment, when the bending operation lever 30 of the wire operating section 26 of the operation section 3 is operated to be rotated, one angle wire 16 among the pair of the angle wires 16 is pulled and the other angle wire 16 is slacked. The active bending section 12 is therefore bent toward the angle wire 16 pulled. The illumination window 7, the observation window 8 and the channel outlet port 9 of the distal end rigid section 6 can thereby be turned in a desired direction.

In order to shift the bend radius R of the bending section 5 as in the case where the endoscope 1 should be inserted into either bronchus, the bend-form setting lever 35 of the actuation pipe operating section 27 is operated. When the actuation pipe 25 is operated to be pushed toward a side of the active bending section 12 by the operation of the bend-form setting lever 35, the gap S is narrowed. At this point, in a state that the actuation pipe 25 compresses the front side coil 23, the angle coil 21 can attain sufficient rigidity by the tightness of the actuation pipe 25 in the entire passive bending section 13. In this case, as the rigidity of the passive bending section 13 can be shifted so that the rigidity of the passive bending section 13 can increase, if the bending operation lever 30 is operated and the one angle wire 16 is pulled, the active bending section 12 will be mainly bent. As a result, the bending form of the passive bending section 13 can be shifted at a large bend radius R as shown at (I) in FIG. 5, so that the passive bending section 13 prevents from bending with the bendable active bending section 12.

When the bend-form setting lever 35 is operated, and the actuation pipe 25 is pulled toward a side of the operation section 3, the gap S is greatly widened. In a state that the actuation pipe 25 is not abutted on the front side coil 23, rigidity of the angle coil 21 of the passive bending section 13 decreases by the non-tightness of the actuation pipe 25. In this case, as the rigidity of the passive bending section 13 can be shifted so that the rigidity of the passive bending section 13 can decrease, if the bending operation lever 30 is operated and the one angle wire 16 is pulled, the passive bending the section 13 can be bent. As a result, the bending form of the passive bending section 13 can be shifted at a smaller bend radius R as shown at (III) in FIG. 5, so that the passive bending section 13 can bend together with the active bending section 12.

Moreover, when the bend-form setting lever 35 is operated, the actuation pipe 25 is moved to the midpoint between the front side coil 23 and the rear side coil 24. The bending form of the passive bending section 13 can be shifted at the intermediate bend radius R as shown at (II) in FIG. 5.

(Advantages)

The configuration described above is advantageous in the following respects. In using the endoscope 1 according to the embodiment, when the bend-form setting lever 35 of the actuation pipe operating section 27 is operated, and the bending shape adjusting section 22 is driven, the bending form of the passive bending section 13 which is curved by an external load is shifted in a desired shape.

The endoscope operator can shift the bending form of the passive bending section 13 in an intended state. As the passive bending section 13 is permitted to be bent or to not permitted to be bent, the bend radius R of the bending section 5 including the active bending section 12 and the passive bending section 13 can be changed. In a case that the bronchoscope which should be inserted into a bronchus is used, when the bronchoscope is inserted from a branching bronchus into an upper lobe bronchus with a large bending angle at a nerve center, the bend-form setting lever 35 is operated, the actuation pipe 25 is pushed toward a side of the active bending section 12, and the bend radius R of the passive bending section 13 is shifted at an increased state as shown at (I) in FIG. 5. When the bronchoscope is inserted into a periphery of the lung, the bend-form setting lever 35 is operated, the actuation pipe 25 is pulled toward a side of the operation section 3, and the bend radius R of the passive bending section 13 is shifted at a decreased state as shown at (III) in FIG. 5. The efficiency of inserting the insertion section 2 of the endoscope 1 can thus be enhanced.

In this embodiment, the distal end of the actuation pipe 25 is a changing point of the rigidity of the passive bending section 13. The passive bending section 13 can therefore be bent at any part, merely by moving the actuation pipe 25 back or forth in an axial direction of the insertion section 2.

In this embodiment, the reinforcing coil 42 wound around the outer circumferential surface of the instrument insertion channel 41 is changed in rigidity depending on a location of the bending section 5. The first reinforcing coil section 42a which is more flexible than the reinforcing coil 42 of the standard stiffness is provided in the part corresponding to the distal part X of the bending section 5. At the first reinforcing coil section 42a which corresponds to the distal part X of the bending section 5, the instrument insertion channel 41 is hardly clamped between the wire guide 50 and the forceps. The distal part of the bending section 5 is hardly bent because it is the last to bend. Hence, a bending force which the distal part of the bending section 5 is bent can be reduced, as the hardness of the first reinforcing coil section 42a can be made flexible and the instrument insertion channel 41 can be made flexible.

The second reinforcing coil part 42b which is harder than the reinforcing coil of the standard hardness is provided in the part corresponding to the middle section Y of the bending section 5. At the second reinforcing coil 42b which corresponds to the middle section Y of the bending section 5, the instrument insertion channel 41 may be clamped between the wire guide 50 and the forceps because the force for inserting the forceps is large. A contact rate which the channel 41 and the wire guide 50 are contacted can be reduced, as the stiffness of the second reinforcing coil section 42b can be made hard and a change of form of the channel 41 can be suppressed. As a result, the channel 41 is less worn than otherwise, easily kept in the bent form, the forceps is be easily guided to the target part. Since the second reinforcing coil part 42b is arranged at the position where the wire guide 50 contacts the channel 41, it prevents the channel 41 from collapsing between the forceps and the wire guide 50 more effectively than otherwise.

Further, the third reinforcing coil part 42c which is more flexible than the reinforcing coil of the standard stiffness is provided in the part corresponding to the proximal section Z of the bending section 5. At the first reinforcing coil part 42c which corresponds to the proximal section Z of the bending section 5, the channel 41 is hardly clamped between the wire guide 50 and the forceps. A bending force which the proximal part of the bending section 5 is bent can be reduced, as the rigidity of the third reinforcing coil unit 42c can be made flexible and the channel 41 can be made flexible since the bending section 5 starts bending at the proximal end thereof.

As described above, the reinforcing coil 42 wound around the outer circumferential surface of the instrument insertion channel 41 is different in rigidity depending on locations of the bending section 5, and the stiffness of the channel 41 corresponding to the bending section 5 is shifted depending on the locations of the bending section 5. The structure of the instrument insertion channel 41 corresponding to the bending shape of the bending section 5 is optimized. Hence, the instrument insertion channel 41 can be improved in durability, the endoscope 1 can be improved in operability, and the physical burden of the user can be reduced.

Second Embodiment (Configuration)

Figure 8:
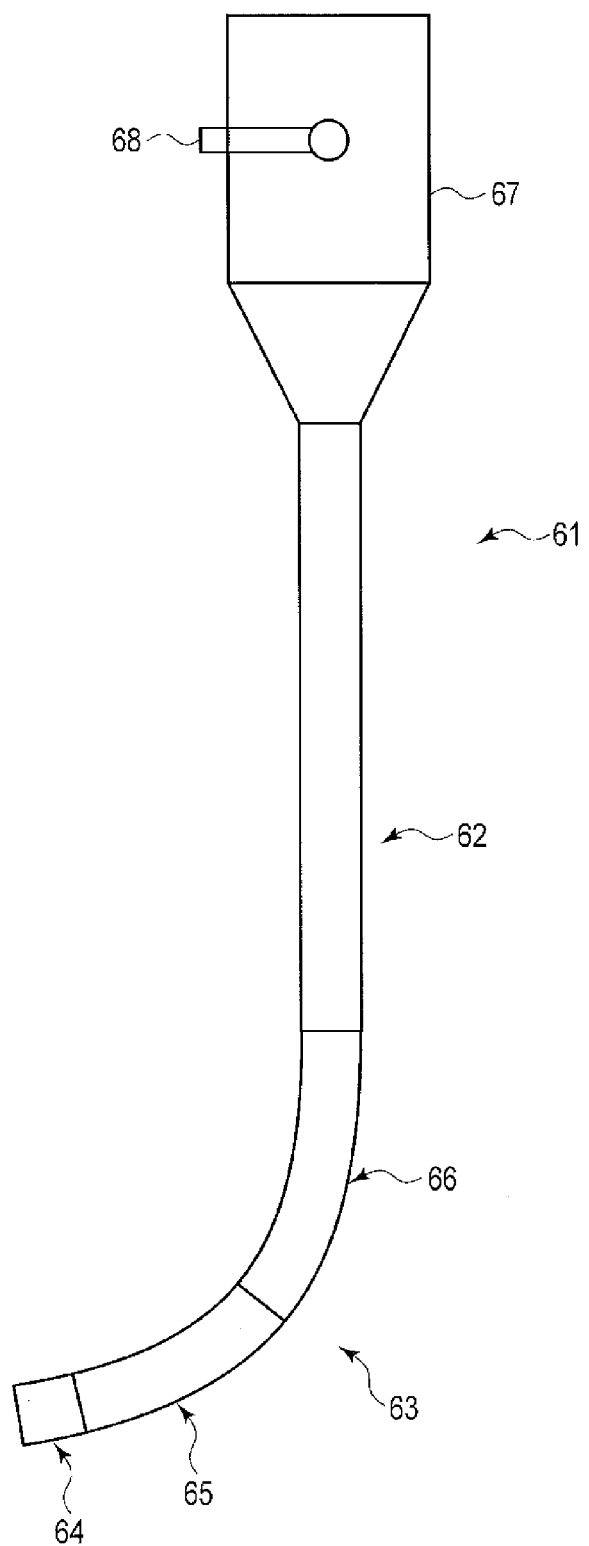
FIG. 8 is a side view showing a rigid endoscope of a second embodiment of the invention.

FIG. 8 shows a second embodiment of this invention. The first embodiment (see FIG. 1A to FIG. 7) is the small-diameter flexible endoscope 1, such as a bronchoscope. By contrast, the present embodiment is a rigid endoscope 61. The rigid endoscope 61 includes a bending section 63 which can be bent and is secured to the distal end of the insertion section 62 which is a hard member such as a metal tube, and a distal end rigid section 64 which is secured to the most distal end of the insertion section 62.

In this embodiment, the bending section 63 includes an active bending section (first bending section) 65 which is provided on the distal end part thereof and can be bent in any direction desired, and a passive bending section (second bending section) 66 which is provided to the proximal end of the active bending section 65 and is held in a condition permitting bending by an external force. The bendable part 65 is similar, in configuration, to the active bending section 12 of the first embodiment. The bended part 66 is also similar, in configuration, to the passive bending section 13 of the first embodiment.

A bending operation lever (bending operation section) 67 operated to bend the bending section 63 and a bend-form setting lever (shift operation section) 35 (see FIG. 4) which is operated to set a bending shape of the passive bending section 66 are provided on an operation section 67 coupled to the proximal end of the insertion section 62. If the bending operation lever 68 of the operation section 67 is operated to be rotated, the active bending section 65 will be bent.

If the bend-form setting lever 35 is operated, the passive bending section 66 which is passively bent with an external load is changed with the arbitrary bending form, in the same manner as in the first embodiment.

(Operation and Advantages)

Although this embodiment is a rigid endoscope 61, the bending part 63 includes a bendable part 65 that can be arbitrarily bent, and a bended part 66 that is secured to the proximal end of the bendable part 65 and held in a condition permitting passively bending by an external force. The bended part 66 passively bent with an external load is changed with the arbitrary bending form, in the same manner as in the first embodiment. Hence, about the bending part 63 of the rigid endoscope 61, this embodiment can achieve advantages similar to those of the first embodiment.

The present invention is not limited to the embodiments described above. Accordingly, various modifications may be made without departing from the spirit or scope of the general inventive concept as defined by the appended claims and their equivalents.

The other technical items characterizing this invention will be described below:

(Item 1) An endoscope includes: a bendable part provided at the distal part of a bending section and operated to be arbitrarily bent; and a banded part provided at the proximal end of the bendable part and held in a condition permitting passively bending by an external force, wherein the bended part includes a bending shape adjustment section which arbitrarily adjusts the bending shape.

(Item 2) The endoscope of Item 1, wherein the bending shape adjustment section includes a bending rigidity changing mechanism which is configured to arbitrarily change the bending rigidity, and configured to arbitrarily shift the bending form.

(Item 3) The endoscope of Item 2, wherein the bending shape adjustment section includes an actuation pipe interposed between an angle wire extending in the bended part and a wire guide unit guiding the angle wire and supported to move in an extending direction of the wire guide unit, and the rigidity of the bended part is configured to be shifted to any conditions.

(Item 4) The endoscope of Item 3, includes an operation section connected to the proximal end of the insertion section, including a wire manipulating section configured to pull the angle wire and an actuation-pipe operating unit configured to pull the actuation pipe, and the bending shape adjustment section is configured to arbitrarily shift the bending shape of the bended part when the actuation pipe is pulled by the actuation-pipe operation unit.

(Item 5) The endoscope of Item 4, wherein the wire guide unit includes a front side wire guide section and a rear side wire guide section, which are spaced apart from each other in the bended part, a distal end of the front side wire guide section is secured to a distal end of the bended part, a rear end of the front side wire guide part is extended in the bended part for a given distance, the rear side wire guide part is secured to a rear end of the bended part, a rear end of the rear side wire guide part is extended to a rear end of the insertion section, the actuation pipe is inserted into the rear side wire guide part, a length of the actuation pipe is as long as, or longer than the rear side wire guide section, an outer diameter of the actuation pipe is as large as, or larger than an inner diameter of the front side wire guide section, and the bending shape adjustment section is configured to arbitrarily shift the stiffness of the bended part when the actuation pipe is moved to the extending direction of the wire guide part with a gap between the front side wire guide and the rear side wire guide.

(Item 6) The endoscope of Item 4, wherein the bending shape adjustment section is configured to shift a state that the bending form of the bended part is configured to form of a small bend radius R when the actuation pipe operating section is operated and the actuation pipe is pulled to a side of the operation section, and a state that the bending form of the banded part is configured to form of a large bend radius R when the actuation pipe operating section is operated and the actuation pipe is pushed to a side of the bendable part.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
    an elongate insertion section in which an angle wire is inserted and that includes a bending section which is configured to be bent by applying a traction force to the angle wire;
    a bending operation section configured to operate a bending of the bending section;
    a shift mechanism configured to shift a bend radius of the bending section depending on the bending operation section; and
    a shift operation section configured to arbitrarily operate the shift mechanism, wherein
    the bending section comprises an active bending section which is disposed at a distal side of the bending section and which is configured to bend and a passive bending section which is disposed proximally from the active bending section and which is passively bent with an external force,
    the shift mechanism is provided in the passive bending section and comprises:
    coil-shaped front and rear wire guides which are respectively secured to the insertion section, wherein a proximal end of the front wire guide is axially separated from a distal end of the rear wire guide and is closer than the distal end of the rear wire guide to a distal end of the insertion section, and the angle wire being inserted and guided through the front and rear wire guides, and
    an actuation pipe which is configured to insert and guide the angle wire, which is formed as a concentric cylinder of the angle wire, which is inserted into the rear wire guide, a distal end of the actuation pipe being slidable in the extending direction of the angle wire between the rear wire guide and the proximal end of the front wire guide depending on an operation of the shift operation section, and the actuation pipe being configured to adjust a gap between the proximal end of the front wire guide and the distal end of the actuation pipe,
    a rigidity of the passive bending section is configured to be shifted depending on a position of the distal end of the actuation pipe with respect to the rear wire guide while the actuation pipe is moved in the extending direction of the angle wire, and
    a bend radius of the passive bending section is defined by the gap between the proximal end of the front wire guide and the distal end of the actuation pipe.

2. The endoscope according to claim 1, wherein the shift mechanism is configured to shift between a first state in which the active bending section is bent together with the passive bending section when the bending operation section is operated, and a second state in which the active bending section is bent and the passive bending section is prevented from being bent when the operation section is operated.

3. The endoscope according to claim 2, wherein the shift mechanism is configured to shift the rigidity of the passive bending section in the first state that the passive bending section is bent when the bending operation section is operated, and in the second state that the passive bending section is prevented from being bent when the bending operation section is operated.

4. The endoscope according to claim 1, wherein the front wire guide is secured to a distal end of the passive bending section,
    the proximal end of the front wire guide extends proximally in the passive bending section,
    the rear wire guide is secured to a proximal end of the passive bending section, and
    a proximal end of the rear wire guide extends proximally to a proximal end of the insertion section.

5. The endoscope according to claim 1, wherein a length of the actuation pipe is as long as, or longer than, the rear wire guide, and
    an outer diameter of the actuation pipe is equal to or larger than an inside diameter of the front side wire guide.

6. The endoscope according to claim 1, wherein the actuation pipe is made of a metal.

* * * * *